United States Patent [19]

Murakami et al.

[11] Patent Number: 4,467,654

[45] Date of Patent: Aug. 28, 1984

[54] ULTRASONIC FLAW DETECTION OF A PIPE

[75] Inventors: Shinichi Murakami, Osaka; Junichi Sugitani, Hirakata; Teruo Yoshimoto, Suita, all of Japan

[73] Assignees: Kubota, Ltd.; Osaka Gas Kabushiki Kaisha, both of Osaka, Japan

[21] Appl. No.: 312,452

[22] Filed: Oct. 19, 1981

Related U.S. Application Data

[63] Continuation of Ser. No. 81,289, Oct. 2, 1979, abandoned.

[51] Int. Cl.³ .............................................. G01N 29/04
[52] U.S. Cl. .......................................... 73/640; 73/644
[58] Field of Search ................. 73/640, 618, 620, 622, 73/624, 633, 637, 638, 644

[56] References Cited

U.S. PATENT DOCUMENTS

| | | | |
|---|---|---|---|
| 3,248,933 | 5/1966 | Stebbins | 73/640 |
| 3,302,453 | 2/1967 | Wood et al. | 73/622 |
| 3,930,404 | 1/1976 | Ryden, Jr. | 73/622 |
| 4,041,773 | 8/1977 | Hauldren et al. | 73/638 |

FOREIGN PATENT DOCUMENTS

| | | | |
|---|---|---|---|
| 1075461 | 7/1967 | United Kingdom | 73/640 |
| 1164456 | 9/1969 | United Kingdom | 73/622 |

OTHER PUBLICATIONS

N. P. Aleshin et al., "Signal-to-Noise Enhancement in the Ultrasonic Inspection of Pipe Welds", Soviet Journal of Nondestructive Testing, vol. 11, No. 1, pp. 99–102, Jan.-Feb. 1975.

*Primary Examiner*—Stephen A. Kreitman
*Attorney, Agent, or Firm*—Edwin E. Greigg

[57] ABSTRACT

A method of ultrasonic flaw detection of a pipe, worth particularly for instance for a heater pipe as is used for catalytic gas reforming with steam. A transmitter probe and a receiver probe are disposed on the pipe outer surface with suitable spacing one from the other both in axial or longitudinal direction and in peripheral direction of the pipe. The transmitter probe launches ultrasonic radiation under proper angle of incidence upon the pipe outer surface at the point of entering material of the pipe, to be refracted under a particular angle of refraction so that it may then pass through the material of the pipe straight to another point upon the pipe outer surface. The receiver probe receives the ultrasonic radiation transmission echo. Flaw in the material of the pipe is detected from fluctuation of the echo, as seen upon scanning the pipe surface by moving the transmitter and receiver probes.

1 Claim, 6 Drawing Figures

ULTRASONIC FLAW DETECTION OF A PIPE

This is a continuation of application Ser. No. 81,289, filed Oct. 2, 1979, now abandoned.

BACKGROUND OF THE INVENTION

This invention relates to a non-destructive testing method for detecting long-term degradation of material of pipes, for instance catalytic reforming heater pipes as those used for reforming natural gas with steam, and more particularly to a method of ultrasonic flaw detection of pipes.

Conventionally, double probe type ultrasonic flaw detection of a pipe is made with the pair of probes disposed on the pipe as schematically illustrated in FIG. 6 of the accompanying drawings.

Thus, on outer surface of a pipe 1 defining a longitudinal axis thereof there are disposed a transmitter probe 3 and a receiver probe 4 to always be on a common peripheral circle normal to the longitudinal axis of the pipe 1 but movable as an integral assembly along the outer surface of the pipe 1 for scanning the surface. During such scanning, the transmitter probe 3 launches ultrasonic radiation towards material of the pipe 1, and the receiver probe 4 receives the ultrasonic radiation transmission echo as emerges out of the material of the pipe 1, to thus detect any flaw in the material of the pipe 1 from fluctuation of the echo.

With such conventional method, there is no serious problem in detecting flaws within the parent metal portion of the welded pipe, but it has practically been impossible to effectively detect flaws in an annular weld portion 19 since the transmitter and receiver probes 3,4 should then be placed on the weld bead and too heavy fluctuations appear as noises in the echo to properly detect flaws, because of irregular undulatious of the bead surfaces in the path of the ultrasonic radiation, namely at the points of entrance into and emerging out of the material of the pipe.

SUMMARY OF THE INVENTION

This invention has as its object to overcome the difficulty in the prior art as mentioned above. To attain the object, the ultrasonic flaw detection method for a pipe comprises according to this invention the steps of: disposing a transmitter probe on the pipe outer surface; providing ultrasonic radiation launched by the transmitter probe under proper angle of incidence upon the pipe outer surface, at the point of entering material of the pipe, to be refracted thereupon under a particular angle of refraction so that the refracted ultrasonic radiation may pass through the material of the pipe straight to another point upon the pipe outer surface, spaced a suitable distance from the point of entrance both in axial or longitudinal direction and in peripheral direction of the pipe, to emerge there out of the material of the pipe; disposing a receiver probe on the pipe outer surface for receiving the ultrasonic radiation emerging out of the material of the pipe, thus the transmission echo; and scanning the pipe outer surface by moving the transmitter and receiver probes along the pipe outer surface, keeping the said proper relative disposing relation therebetween.

Since the transmitter and receiver probes are thus disposed according to this invention with suitable spacing one from the other not only in the peripheral direction of the pipe but also in the axial or longitudinal direction thereof, these two probes are positioned, when to detect flaws in an annular weld portion, on the pipe outer surface unaffected by the welding on opposite sides of the weld bead, thus to cause ultrasonic radiation to enter, and emerge out of, the material of the pipe both at the surface unaffected by the welding, whereby it has been made possible to accurately detect flaws even in the weld portion without being affected by irregular undulations of the weld bead outer surface, to say nothing of flaw detection in the normal parent metal portion unaffected by the welding.

Providing ultrasonic radiation launched by the transmitter probe under proper angle of incidence upon the pipe outer surface, at the point of entering material of the pipe, to be refracted thereupon under a particular angle of refraction so that the refracted ultrasonic radiation may pass through the material of the pipe straight to another point upon the pipe outer surface to there emerge out of the material of the pipe, is the well known feature of the direct transmission echo method.

In a preferred embodiment of this invention, the transmitter and receiver probes are provided by means of immersion method technique. With this provision, disturbance of ultrasonic radiation at entering and emerging out of the material of the pipe even as blackwork with the unwrought outer surface, as is commonly the case in austenitic heat resisting cast steel pipes as are used as heater pipes for catalytic gas reforming, is effectively reduced to thus enhance flaw detection accuracy.

Further advantages of this invention will become clear from the detailed description of the preferred embodiment given hereunder with reference to the accompanying drawings.

BRIEF DESCRIPTION OF THE DRAWINGS

FIG. 1 is a perspective view of the pipe with probes used for performing the method of the invention shown schematically, FIG. 2 is a sectional view taken on a plane shown at II—II in FIG. 1 looking in the direction of the arrows, FIG. 3 is a schematic illustration of an apparatus for manually performing the method of this invention.

FIG. 4 is a similar schematic illustration of an apparatus having mechanized scanning system, FIG. 5 is a schematic view of the pipe with the probes disposed according to this invention and FIG. 6 is a schematic view of the pipe similar to FIG. 5 but with the probes disposed in a conventional manner.

DETAILED DESCRIPTION OF THE PREFERRED EMBODIMENT

Figure 1:
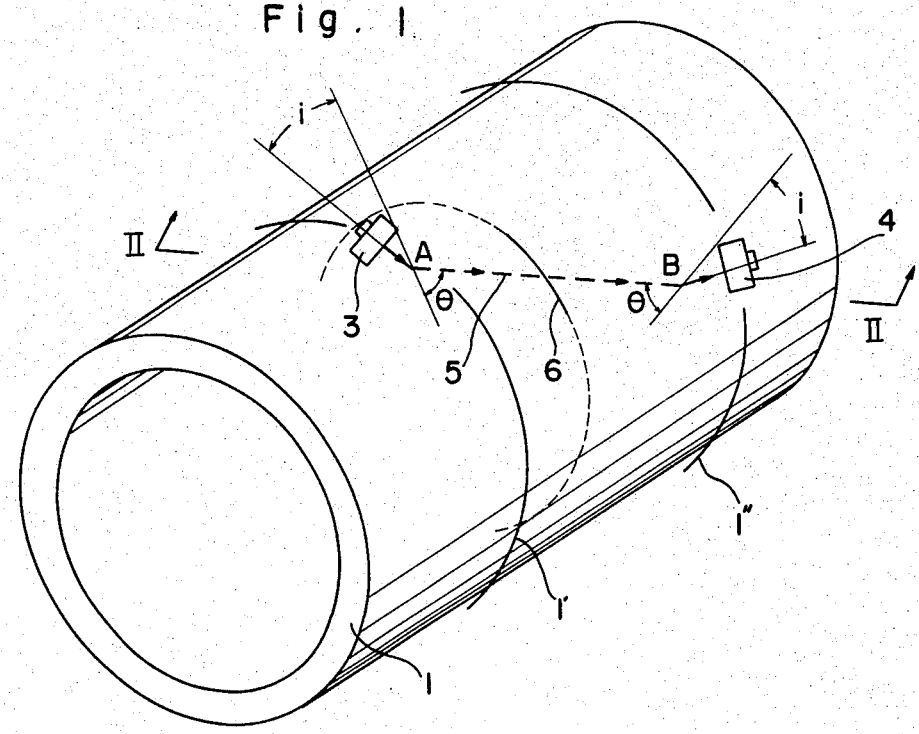
FIGS. 1–5 are various views given for explanation of the principle and the performance of the method of ultrasonic flaw detection of a pipe according to this invention, and more particularly
Figure 2:
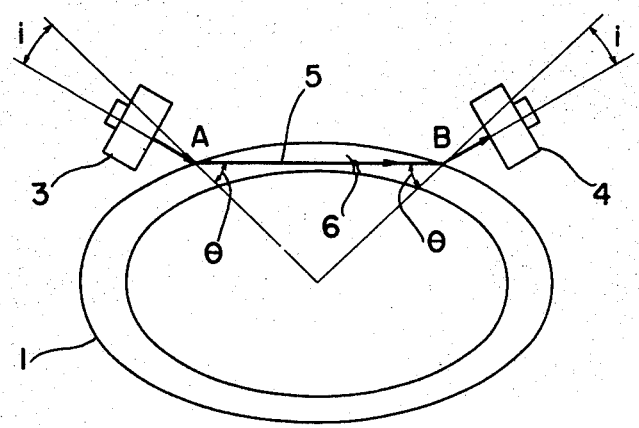

Explaining the principle of this invention with reference to FIGS. 1 and 2, pipe 1 is the object to be inspected, for instance a heater pipe. On the pipe outer surface there are disposed a transmitter probe 3 and a receiver probe 4 with suitable spacing one from the other both in axial or longitudinal direction and in peripheral direction of the pipe 1. Two parallel circles 1' and 1" normal to the pipe axis, passing through the probes 3 and 4, respectively, are shown in FIG. 1 to clearly show the axial as well as peripheral spacing as mentioned above. As shown by the arrows starting from the transmitter probe 3 to the receiver probe 4, ultrasonic radiation 5 is launched by the transmitting probe 3 to enter material of the pipe 1 at a point A on the outer surface thereof under proper angle of incidence i, to then be refracted under a particular angle of refraction and to pass straight through the pipe material to another point B on the outer surface thereof to thereupon be refracted in a manner the same as at the entrance point A and to emerge out of the pipe material for reception of such transmission echo by the receiver probe 4. Accordingly, if a flaw 6 extending in the peripheral direction of the pipe 1 as shown in FIG. 1 is present in the pipe material in the way of the said straight path through the material from the point A to the point B, thus within the sectional plane shown in FIG. 2 with elliptic section of the pipe 1, then the flaw is detected as the corresponding attenuation of the transmission echo as received by the receiver probe 4, and the shape and dimension of the flaw 6 in the pipe peripheral direction can clearly be identified by scanning the pipe outer surface by moving the transmitter and receiver probes 3 and 4 along the pipe outer surface, keeping the said proper relative disposing relation therebetween, since the direction of propagation of the ultrasonic radiation 5 and the flaw 6 extending in the peripheral direction of the pipe 1 are in non-parallel, crossing relation with each other. Flaws extending in the axial or longitudinal direction of the pipe 1, if any, can also clearly be detected and identified, just the same as above. In so causing the ultrasonic radiation 5 to enter, and emerge out of, material of the pipe 1, it is here supposed to provide the transmitter probe 3 and the receiver probe 4 by means of immersion method technique, to thereby minimize the disturbance by unevenness or irregular undulations of the outer surface of the pipe 1.

Figure 5:
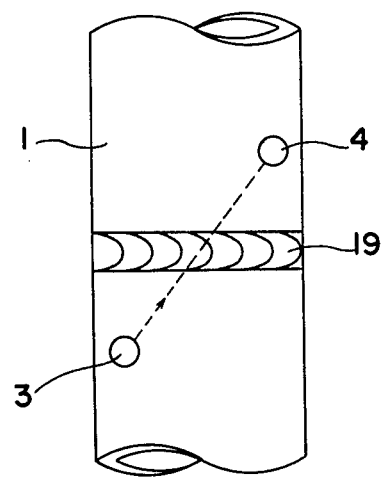
Figure 6:
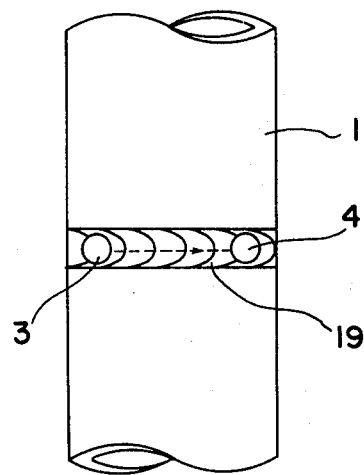

Since the transmitter and receiver probes 3,4 are thus disposed according to this invention with spacing one from the other in the axial or longitudinal direction of the pipe 1, these two probes 3,4 are positioned, when to detect flaws in an annular weld portion 19 as shown in FIG. 5, on the pipe outer surface unaffected by the welding on opposite sides of the weld bead. It has thereby thus been made possible to make the flaw detection even in the weld portion 19 without being affected by irregular undulations of the weld bead outer surface, not to mention flaw detection in the normal parent metal portion unaffected by the welding.

Figure 3:
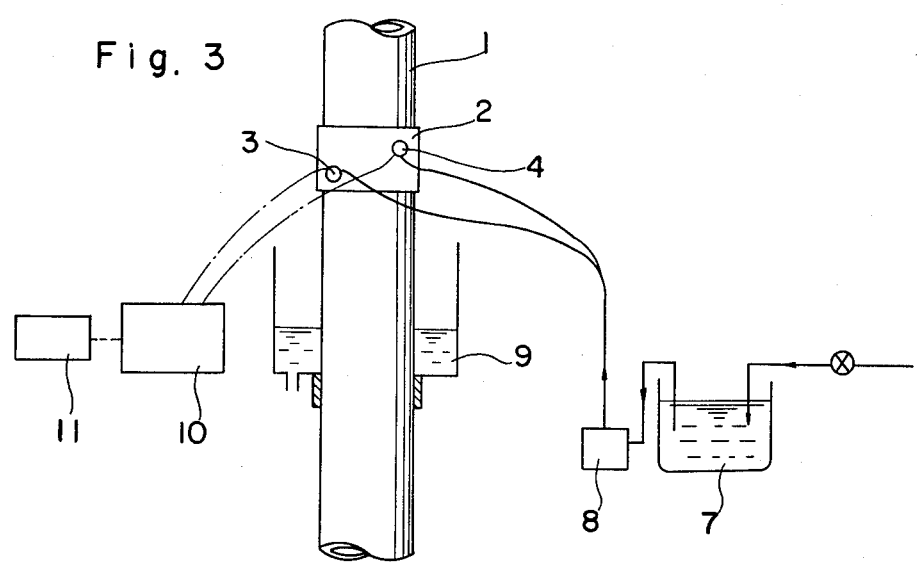

FIG. 3 shows an embodiment of an apparatus for performing the method of this invention, with a pipe 1 as the object to be inspected. Generally designated at 2 is an adaptor assembly fitted on the pipe 1 to be movable therealong, and it accommodates therein a transmitter probe 3 and a receiver probe 4. In order to provide both of the probes 3,4 by means of immersion method technique, water is supplied from a tank 7 by a pump 8 to fill gaps between the probes 3,4 and the pipe outer surface portions thereunder, to make up proper passageways of the ultrasonic propagation. Water as may possibly leak out of the adapter 2 along the pipe outer surface is received in a reservoir 9 liquid-tightly fitted on the pipe 1 on a level lower than the adaptor 2, and is properly discharged out therefrom so that trouble by flowing-down of leak water may be eliminated even if the pipe 1 under inspection is installed in a heating oven. As is well known in the art, the probes 3,4 are connected with a flaw detector unit 10, so that the transmitter probe 3 may launch ultrasonic radiation and the receiver probe 4 may receive the transmission echo through material of the pipe 1 without reflection on the inner surface thereof, as was described with respect to FIGS. 1 and 2, and the echo may be visualized on a CRT (cathode ray tube) provided as a component of the flaw detector unit 10. As is shown in FIG. 3, a recorder 11 may also be provided, as connected to the flaw detector unit 10, for recording the echo pattern.

Figure 4:
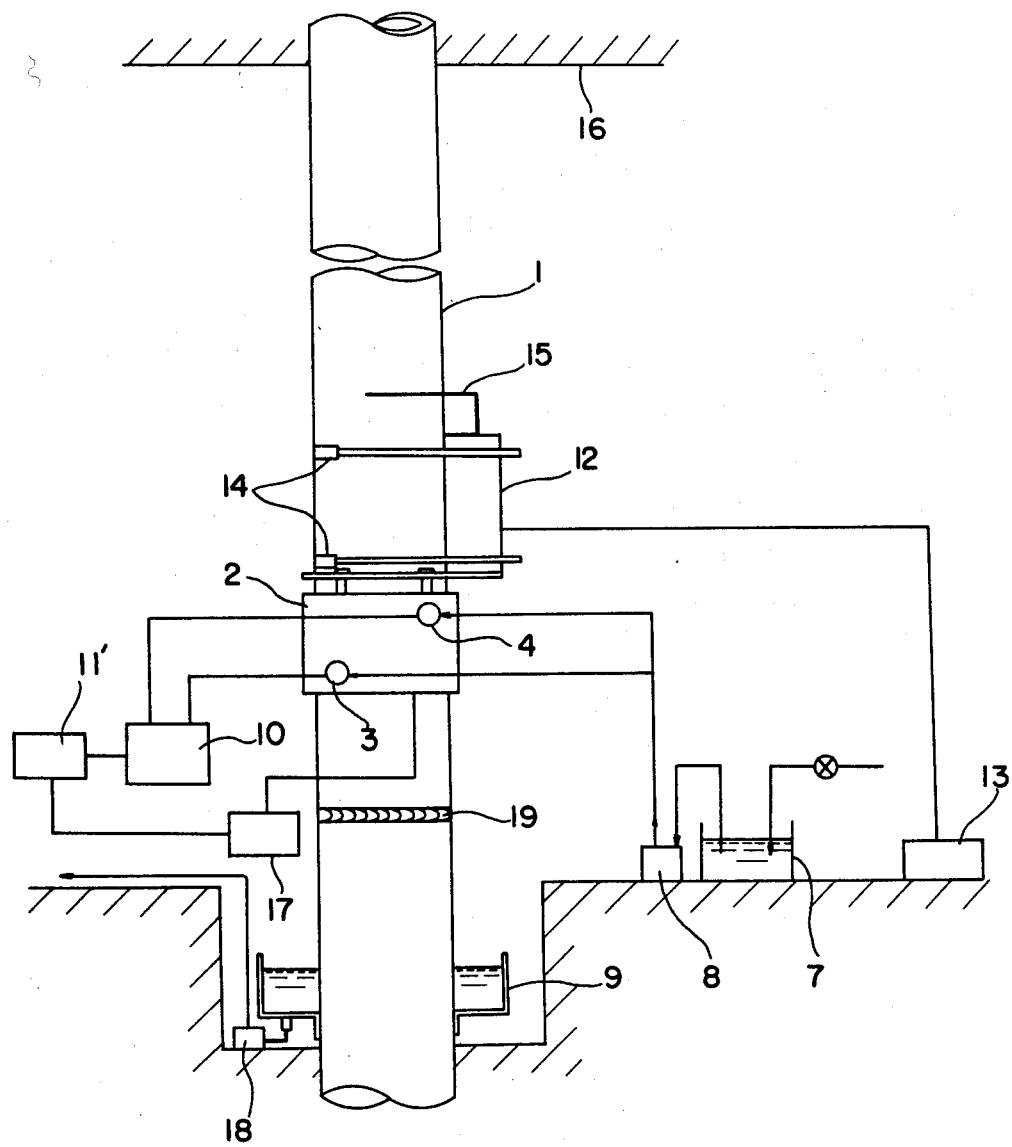

Though the apparatus shown in FIG. 3 is of the type for manual operation, the method of this invention may as well be performed by apparatuses having mechanized scanning system, of which a preferred embodiment is shown in FIG. 4. Like parts as shown in FIG. 3 are designated by like reference numerals also in FIG. 4, and no particular explanation is needed with respect to such parts.

Shown schematically at 12 in FIG. 4 is a mechanized scanner connected to the adaptor 2 to move integrally therewith both in axial or longitudinal direction and in peripheral direction of the pipe 1, responsive to maneuvering an operation box 13. The scanner 12 is further equipped with clampingly attaching means 14 for retaining the scanner 12 in embracing relationship on the pipe 1 and with feeler antenna means 15 for automatically ending the upward scanning movement. Thus, the scanner 12 is adapted to automatically end the upward scanning movement upon hitting oven ceiling 16 by the feeler antenna 15. In the instance of FIG. 4 it is supposed that a modified recorder 11' is incorporated, here referred to as modified in that in contrast with the simple one-pen type recorder 11 of FIG. 3 for recording only the ultrasonic transmission echo pattern, this recorder 11' is of two-pen type for recording not only the transmission echo pattern but also roughness of the outer surface of the pipe parent metal or undulations of the weld bead surface, as sensed by suitable means such as a differential transformer type sensor (not illustrated in FIG. 4 but a connection wire to the amplifier 17 just to be referred to is shown) incorporated within the adaptor 2, the output signal of the sensor being given to the recorder 11' via an amplifier 17. Designated at 18 is a pump for discharging out of the oven, or draining, the water received in the reservoir 9.

In contrast with the conventional system with which it is required to set up proper scaffolding within a tall heating oven and to have a specialist operator ascend the scaffolding to manually effect the scanning movement while paying proper care especially when passing over any annular weld bead portion of the pipe 1 (particularly apt to contain flaws) during the scanning movement, the apparatus having the mechanized scanner system and surface unevenness sensor means, as shown in FIG. 4, has the advantage of dispensing with such need of scaffolding and the specialist operator and of automatically sensing the delicate weld bead portion.

We claim:

1. A method of ultrasonic flaw detection of a pipe including a peripheral weld, comprising the steps of:
disposing a transmitter probe and a receiver probe adjacent the outer surface of a vertically standing pipe and suitably spaced from each other both in axial direction and in peripheral direction of the pipe,
continuously supplying water between said probes and the pipe outer surface,
receiving the supplied water flowing down the outer surface in a reservoir disposed downwardly and peripherally of the pipe, providing ultrasonic radiation launched by the transmitter probe under proper angle of incidence into the pipe so that the ultrasonic radiation may pass straight from one point on the pipe outer surface through the material of the pipe and the peripheral weld to another point on the pipe outer surface, the ultrasonic radiation emerging out of the pipe being received by the receiver probe, and scanning the pipe outer surface by a self-propelled scanner which moves the transmitter and receiver probes along the pipe outer surface keeping the proper relative disposing relation therebetween and which automatically stops upon contact with an object.

* * * * *